United States Patent
Moyer et al.

(10) Patent No.: US 8,204,601 B2
(45) Date of Patent: Jun. 19, 2012

(54) CRANIAL ELECTROSTIMULATION DEVICE FOR TREATMENT OF POLYSUBSTANCE ADDICTION AND METHOD OF USE

(75) Inventors: Eric P. Moyer, Huntington Beach, CA (US); Joseph R. Winston, Chapel Hill, NC (US)

(73) Assignee: Seaboard Assets Corp., Medford, NJ (US)

( * ) Notice: Subject to any disclaimer, the term of this patent is extended or adjusted under 35 U.S.C. 154(b) by 333 days.

(21) Appl. No.: 12/582,574

(22) Filed: Oct. 20, 2009

(65) Prior Publication Data
US 2010/0100155 A1    Apr. 22, 2010

Related U.S. Application Data

(60) Provisional application No. 61/116,732, filed on Nov. 21, 2008, provisional application No. 61/106,660, filed on Oct. 20, 2008, provisional application No. 61/106,667, filed on Oct. 20, 2008.

(51) Int. Cl.
*A61N 1/00* (2006.01)
(52) U.S. Cl. .................................................... 607/58
(58) Field of Classification Search .............. 607/58
See application file for complete search history.

(56) References Cited

U.S. PATENT DOCUMENTS

| | | | |
|---|---|---|---|
| 4,232,680 A | 11/1980 | Hudleson et al. | |
| 4,459,989 A | 7/1984 | Borkan | |
| 4,505,275 A | 3/1985 | Chen | |
| 4,520,825 A | 6/1985 | Thompson et al. | |
| 4,598,713 A | 7/1986 | Hansjurgens et al. | |
| 4,646,744 A * | 3/1987 | Capel | 607/58 |
| 4,671,286 A | 6/1987 | Renault | |
| 4,719,922 A | 1/1988 | Padjen et al. | |
| 4,793,353 A | 12/1988 | Borkan | |
| 4,832,033 A | 5/1989 | Maher | |
| 4,865,048 A | 9/1989 | Eckerson | |
| 4,919,139 A | 4/1990 | Brodard | |
| 4,926,865 A | 5/1990 | Oman | |
| 5,012,808 A | 5/1991 | Stubbers et al. | |
| 5,072,730 A | 12/1991 | Lee | |
| 5,163,444 A | 11/1992 | Braverman | |
| 5,593,432 A | 1/1997 | Crowther et al. | |
| 7,041,096 B2 * | 5/2006 | Malis et al. | 606/34 |
| 2007/0093870 A1 | 4/2007 | Maschino | |
| 2007/0233193 A1 | 10/2007 | Craig | |

OTHER PUBLICATIONS

International Preliminary Report on Patentability, dated Apr. 26, 2011, issued in corresponding International Application No. PCT/US2009/061346.

* cited by examiner

*Primary Examiner* — George Manuel
(74) *Attorney, Agent, or Firm* — Saul Ewing LLP

(57) ABSTRACT

The cranial electrostimulation devices described herein are suitable for use in detoxification from and amelioration of the symptoms of acute and chronic withdrawal from simultaneous multiple addictive substances by transcutaneous electric nerve stimulation. A plurality of time-division multiplexed analog waveforms is applied to the mastoid process of a person in need thereof, thereby treating symptoms of withdrawal from addictive substances. The invention also provides a protocol for encoding a plurality of different waveforms combined sequentially or simultaneously, as well as an improved cranial electrostimulation apparatus having a stable output waveform signal over the useful service life of the power supply, e.g., the battery.

17 Claims, 13 Drawing Sheets

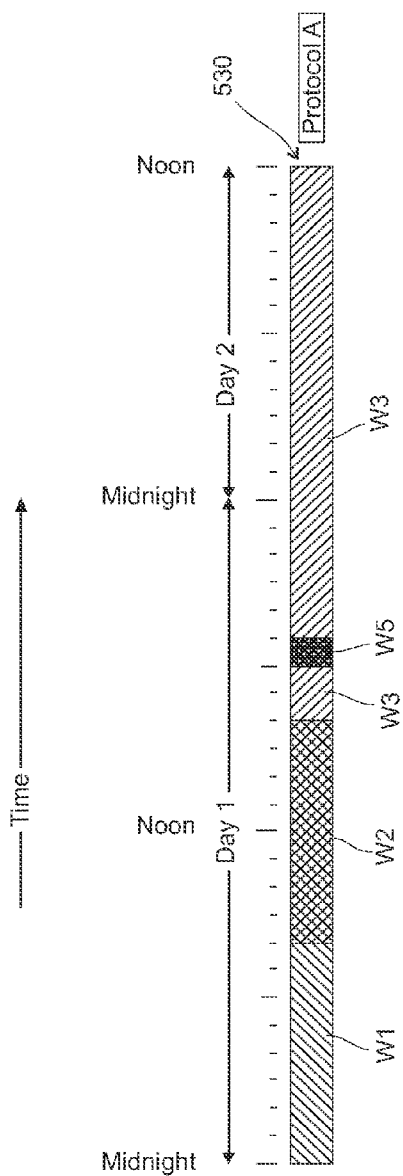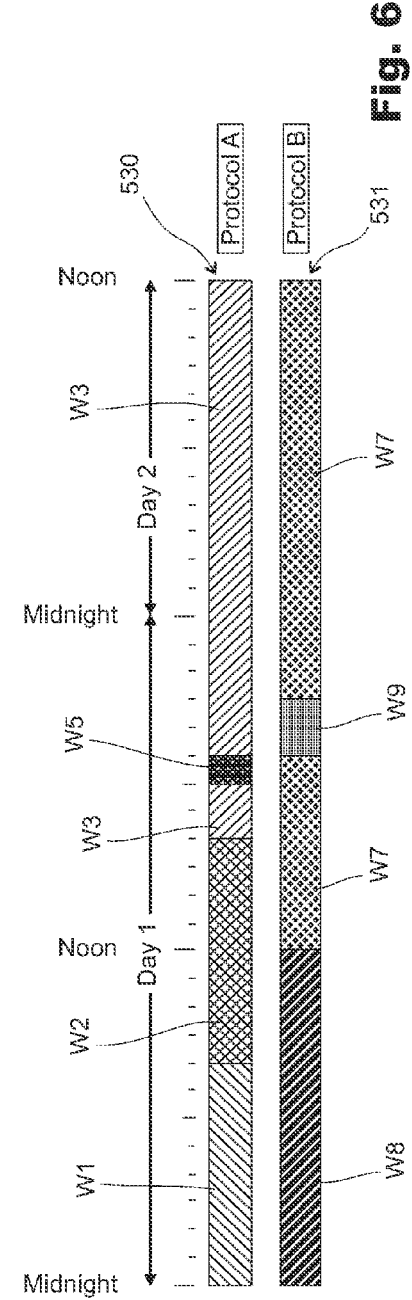

CRANIAL ELECTROSTIMULATION DEVICE FOR TREATMENT OF POLYSUBSTANCE ADDICTION AND METHOD OF USE

CROSS-REFERENCE TO RELATED APPLICATIONS

This application claims the priority of U.S. 61/106,660 (filed on Oct. 20, 2008), U.S. 61/106,667 (filed on Oct. 20, 2008), and U.S. 61/116,732 (filed on Nov. 21, 2008). The entire contents of these three priority applications are incorporated herein by reference.

FIELD

This application describes a cranial electrostimulation device for the treatment of polysubstance addiction and methods of use thereof.

BACKGROUND

Substance-abuse disorders are caused by the use of various types of addictive substances, including drugs of abuse. Millions of persons worldwide are believed to be drug abusers suffering from substance-related disorders. Substance-related mental disorders produce a high cost to society, including socially dysfunctional people, criminal activity, and increased costs of medical care. Thus, there is a worldwide demand for effective treatments of substance-related disorders.

Whereas historically only a relatively small number of drugs were available in local communities, e.g., drugs that could be produced locally, worldwide global commerce has made it possible for a wide variety of drugs to be available locally. As a consequence, it has recently been recognized that persons may be addicted to several substances at the same time. This phenomenon is known as "polysubstance" abuse or addiction. Polysubstance drug users often do not have a particular drug of choice, but rather are addicted to not being sober. While a variety of protocols exist for the medical treatment of addiction to a single substance, there are relatively few effective protocols for the medical treatment of polysubstance abuse. A need exists for innovative methods of treating polysubstance abuse and addiction.

At the onset of any substance-related addiction, the central nervous system ("CNS") reward system is stimulated. The reward system has been identified as the site responsible for intracranial self stimulation, and it plays a role in eliciting senses of pleasure, motivation, and euphoria. The treatment of drug dependence can be made very difficult because many addictive substances stimulate this system, thereby eliciting senses of pleasure in users. This influence remains even after the drug, as a causative agent, is depleted from the body.

Cranial electrostimulation ("CES") has been used to treat addiction by electronically modulating the CNS reward system in addicted persons. CES devices typically deliver low levels of AC current across the head in order to modulate the dopaminergic, serotonergic, and other neurotransmitter systems in the brain for the purposes of affecting anxiety, stress, and addictive behaviors. When used for addiction, CES devices typically produce a series of waveforms that vary in shape, frequency, pulse width, or other attributes in order to target a variety of acute and chronic withdrawal symptoms. The selection and timing of those various waveforms constitute "protocols" that may be targeted towards different addictive substances (e.g., heroin, cocaine, methadone, alcohol, nicotine, etc). For example, U.S. Pat. Nos. 4,865,048 and 5,593,432, which are incorporated herein by reference, both describe protocols and devices that use electronic neurostimulation to treat addiction to a single substance. While effective single-substance protocols have been developed, a substantial percentage of substance abusers take multiple substances at the same time creating a need for effective polysubstance protocols. That is, these prior art devices and methods cannot be effectively used in the simultaneous treatment of addiction to multiple substances as is present in polysubstance addiction. Therefore, a continuing and unmet need exists for new and improved devices and methods of use for the treatment of polysubstance addiction. The present invention provides a solution to these problems, among other things.

SUMMARY

The cranial electrostimulation devices described herein are suitable for use in detoxification from and amelioration of symptoms of acute and chronic withdrawal from simultaneous multiple addictive substances by transcutaneous electric nerve stimulation. A plurality of time-division multiplexed analog waveforms is applied to the mastoid process of a person in need thereof, thereby treating symptoms of withdrawal from addictive substances. The invention also provides a protocol for encoding a plurality of different waveforms combined sequentially or simultaneously, as well as an improved cranial electrostimulation apparatus having a stable output waveform signal over the useful service life of the power supply, e.g., the battery.

Accordingly, in an embodiment, the invention provides a method of cranial electrostimulation for detoxification from and amelioration of symptoms of acute and chronic withdrawal from simultaneous multiple addictive substances comprising administering a time-division multiplexed plurality of analog waveforms to a person in need thereof, wherein each waveform of the plurality of analog waveforms is defined by an alternating electric current encoding a therapeutic protocol selected for the treatment or prevention of symptoms of addiction to a substance.

In another embodiment, the invention provides an improved cranial electrostimulation apparatus comprising (1) a power supply configured to generate a DC power signal; (2) a signal generator configured to generate a control signal for modulating the power signal corresponding to a waveform adapted to provide therapeutic value to a patient; (3) a voltage regulator coupled to receive the DC power signal from the power supply and output a regulated DC voltage signal; (4) a line driver configured to receive as inputs the control signal and the regulated DC voltage signal and generate an output waveform signal by modulating the regulated DC power signal with the control signal; and (5) electrodes coupled to receive the output waveform signal.

In yet another embodiment, the invention provides a method of encoding a definition of a protocol for generating an analog signal for cranial stimulation comprised of a plurality of different waveforms combined sequentially or simultaneously, the method comprising creating a dataset comprising (1) a first segment defining each waveform of the plurality of waveforms; and (2) a second segment comprising an event definition for each different waveform segment presented without cessation in said analog signal, the event definitions organized sequentially in the dataset according to the relative time at which the corresponding waveform segment starts within the protocol; wherein each event definition comprises (a) a duration field disclosing the duration of said waveform segment; (b) a start_delta field disclosing the start time of the event, start time defined as a delay period following the start time of an immediately preceding event definition in said dataset and by zero for the first event definition in said dataset; and (c) a waveform identifier field identifying one of the plurality of waveforms for the waveform segment.

Additional features may be understood by referring to the accompanying drawings, which should be read in conjunction with the following detailed description and examples.

DESCRIPTION OF THE DRAWINGS

FIG. 5 illustrates another exemplary single substance CES protocol.

FIG. 6 illustrates another exemplary polysubstance CES protocol.

In FIG. 14, the following abbreviations are used: BAT=battery; REG=voltage regulator; POT=potentiometer; GEN=signal generator; MOD=modulator; DRV=line driver.

DETAILED DESCRIPTION

Figure 1:
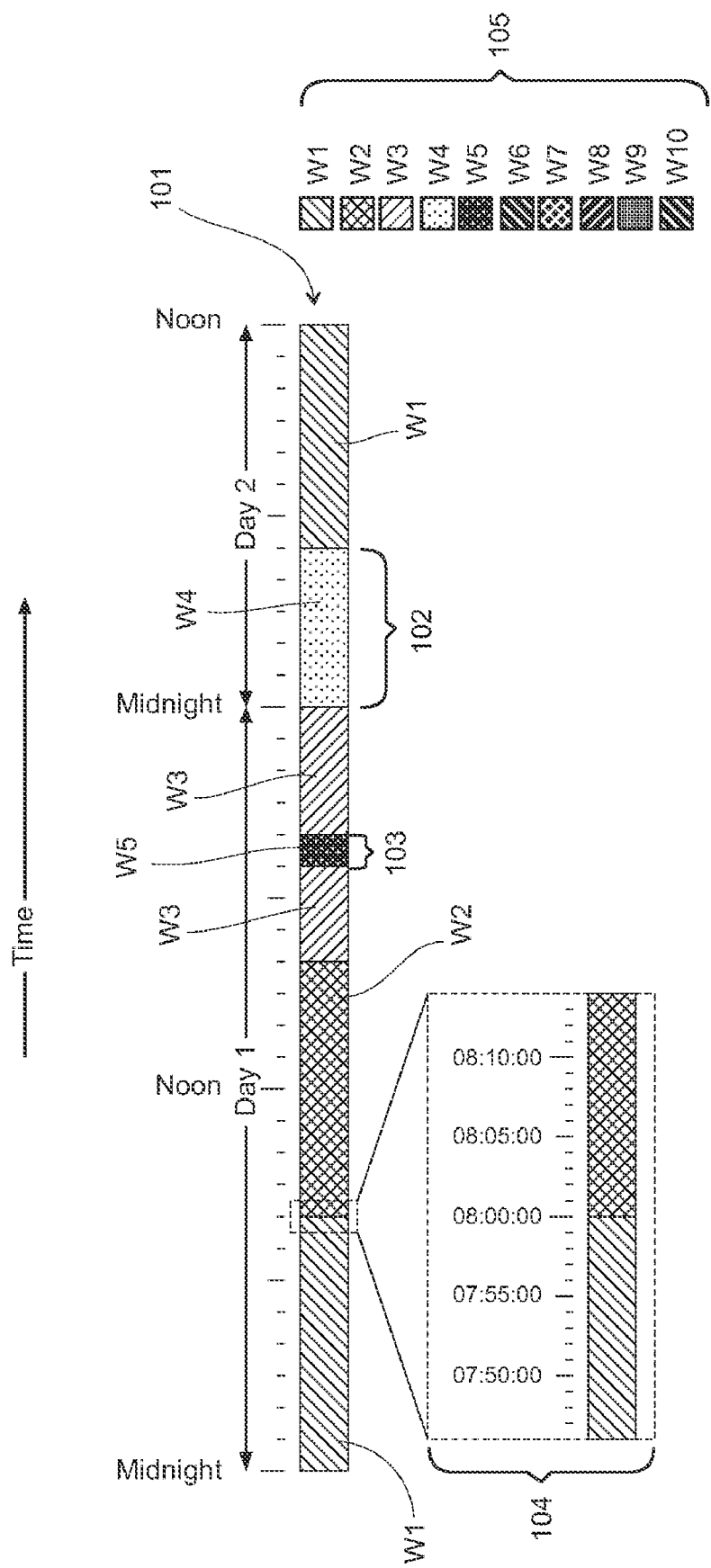
FIG. 1 illustrates an exemplary single substance CES protocol

In an embodiment, the invention provides a method of cranial electrostimulation ("CES") for therapeutic treatment to reduce or remove acute or chronic symptoms of withdrawal from addictive substances comprising administering a time-division multiplexed plurality of analog waveforms to a person in need thereof, wherein each waveform of the plurality of analog waveforms is defined by an alternating electric current encoding a therapeutic protocol selected for the treatment or prevention of symptoms of addiction to a substance. For example, the administering step typically includes at least administering a first time-division multiplexed plurality of analog waveforms, and thereafter administering a second time-division multiplexed plurality of analog waveforms. Additionally, the administering step may include contacting two electrodes to the mastoid process of the person, wherein the plurality of analog waveforms is administered to the person via the electrodes. Each of these features of the invention is discussed below.

Addiction is a chronic, relapsing disease characterized by a loss of control over substance use, compulsive substance seeking, and craving for a substance. Substance use persists despite negative health or social consequences, as well as physical or psychological dependence on the substance. Substance addiction typically follows a course of tolerance, withdrawal, compulsive drug-taking behavior, drug-seeking behavior, and relapse. Substance abuse and addiction are public health issues with significant social and economic impact on both the addict and society by playing a major role in violent crime and the spread of infectious diseases.

Symptoms of addiction include the above-noted behaviors, as well as withdrawal, which refers to the development of a substance-specific maladaptive behavioral change, with physiological and cognitive concomitants, that is due to the cessation of, or reduction in, prolonged substance use. This substance-specific syndrome can cause clinically significant distress or impairment in social, occupational, or other important areas of functioning. The symptoms are not due to a general medical condition and are not accounted for by any other mental disorder. Most persons in withdrawal have a craving to re-administer the substance to reduce the symptoms. The dose and duration of use and other factors such as the presence or absence of additional illnesses also affect withdrawal symptoms.

Some exemplary substances of abuse and addiction include alcohol, caffeine, nicotine, cannabis (marijuana) and cannabis derivatives, opiates and other morphine-like opioid agonists such as heroin and phencyclidine, sedatives such as benzodiazepines and barbiturates, and psychostimulants such as cocaine and amphetamines. Substances may include street drugs, as well as misused ethical (i.e., prescription) drugs.

The present invention treats or prevents the symptoms of withdrawal from polysubstance addiction by administering a CES treatment course of therapy. To be effective, a CES treatment for polysubstance abuse should reflect the addict's substances of addiction, should compensate for variations in the delays between consumption of various substances and the onset of acute withdrawal symptoms, should be sensitive to the time of day (as some CES waveforms enhance sleep while others make sleep difficult), and should weight the protocols' contribution to treatment based on the severity of withdrawal symptoms, personal response to the substances and personal health. Thus, within the limits of sound medical judgment, a unique protocol specific to each person may be prescribed. As further described below, the method of treatment includes administration of a time-division multiplexed plurality of single-substance waveforms to a person in need thereof for the treatment or prevention of symptoms of withdrawal from polysubstance addiction.

The effective combination of multiple single-substance therapeutic protocols, which are generally known in the art, to form a polysubstance protocol is based upon an understanding of several operational aspects of CES, including acute vs. chronic withdrawal symptom management, the time delay between substance consumption and the onset of acute withdrawal symptoms, the relative weighting of CES therapeutic interventions, and night management. Following disuse of an addictive substance, the body experiences acute withdrawal symptoms. With opiates, for example, these symptoms may include cravings, runny nose, stomach cramps, nausea and diarrhea. After the acute phase, chronic withdrawal symptoms may continue for months or years and may include cravings (e.g., visually stimulated cravings) and feelings of dysphoria. For short acting drugs (e.g., heroin, alcohol), the acute symptoms typically begin a few hours after cessation. For long acting drugs (e.g., methadone, valium), the acute symptoms typically begin many hours or several days after cessation. When combining multiple single-substance CES protocols, the algorithm may take into account the relative position in time of the onset of acute symptoms based on short vs. long acting drugs and time of most recent consumption, the relative distress of those symptoms, the impact of certain CES waveforms on sleep patterns (either enabling or disrupting) and their scheduling within the protocol relative to time of day, and the order in which acute and chronic symptoms are addressed by specific waveforms in the combined protocol. The invention provides for a time-division multiplexed plurality of analog single-substance waveforms to be administered for a duration of, for example, from between about 30 minutes to about 14 days, during which time each of these considerations may be addressed.

Time-division multiplexing ("TDM") refers to a process by which multiple unique waveforms, which are characterized by one or more frequencies, pulse widths, amplitudes, or waveform shapes, are transferred apparently simultaneously in one single output signal, with each unique waveform taking turns on the output signal. The time domain is divided into several recurrent timeslots of fixed length, one for each unique waveform (a "sub-channel"). For example, a period of a first unique waveform is transmitted during a first timeslot, a second unique waveform during a second timeslot, and so forth. One TDM frame has one timeslot per unique waveform. After the last waveform the cycle starts all over again with a new TDM frame, starting with another period from unique waveform 1, etc. As illustrated below, the timeslots may be of various time length(s); each timeslot may be of equal or unequal length. When the timeslots are of unequal length, the relative weights of the unique waveforms are reflected in the output signal, and the therapeutic effects of the unique waveforms may be weighted accordingly.

For example, the TDM output signal may include treatment protocols for multiple substances of abuse. In this example, a plurality of analog waveforms includes at least a first waveform and at least a second waveform. The first waveform is administered in timeslots of a first time length, and the second waveform is administered in timeslots of a second time length, the first time length and the second time length being of unequal times. At least one waveform of the plurality of analog waveforms encodes a protocol for the detoxification from and amelioration of the symptoms of acute and chronic withdrawal symptoms of one addictive substance, and at least one waveform of said plurality of analog waveforms encodes a protocol for the detoxification from and amelioration of the symptoms of acute and chronic withdrawal symptoms of a different addictive substance.

The time-division multiplexing process will be better understood by referring to the examples illustrated in FIGS. 1-4. The protocol illustrated in FIG. 1 includes a timeline showing the first 36 hours of a typical single-substance CES protocol. Although only the first 36 hours are illustrated in FIG. 1, such a protocol may typically last for up to 14 days, depending on the drug being treated and the physical condition of the addicted individual. Within any given day, a number of different waveforms may be delivered throughout treatment time domain 101. Each waveform (W1 through W10) 105 may vary by waveshape, frequency, pulse width, modulation, or other characteristics. This example shows a series of waveforms that change during the day, including waveform W4 that is designed to promote sleep being positioned between midnight and 5:00 am in time period 102, and a waveform W5 that is disruptive to sleep being positioned in the afternoon, depicted as time period 103. The transition between waveforms W1 and W2 occurring at 8:00 am on Day 1 is shown in expanded form in inset time domain 104.

In order to combine multiple single-substance CES protocols into a single polysubstance protocol, the single-substance protocols are time division multiplexed. The TDM "stream," which forms the polysubstance protocol, is divided into recurring TDM frames of fixed time lengths. Each TDM frame is subdivided into timeslots of fixed (but not necessarily equal) duration, one for each of the single-substance protocols (i.e., a sub-channel). In the time lines illustrated in FIG. 2, single-substance CES Protocol A 111 and CES Protocol B 112 are combined into a timeline of a poly-substance CES protocol, partially illustrated in inset 113. During the first timeslot, Protocol A is be transmitted, and during the second timeslot, Protocol B is be transmitted. TDM frame length 114 in this example is 5 minutes, and thus each timeslot (one for each of the two sub-channels) is 2.5 minutes long. In this example, between midnight and 8:00 am on Day 1, waveform W1 from Protocol A 115 is time division multiplexed with W8 from Protocol B 116 to form polysubstance protocol 117. At 8:00 am waveform W1 is replaced by W2 in TDM frame 114. Waveforms W2 and W8 accordingly alternate in multiplexed output signal 113.

Figure 2:
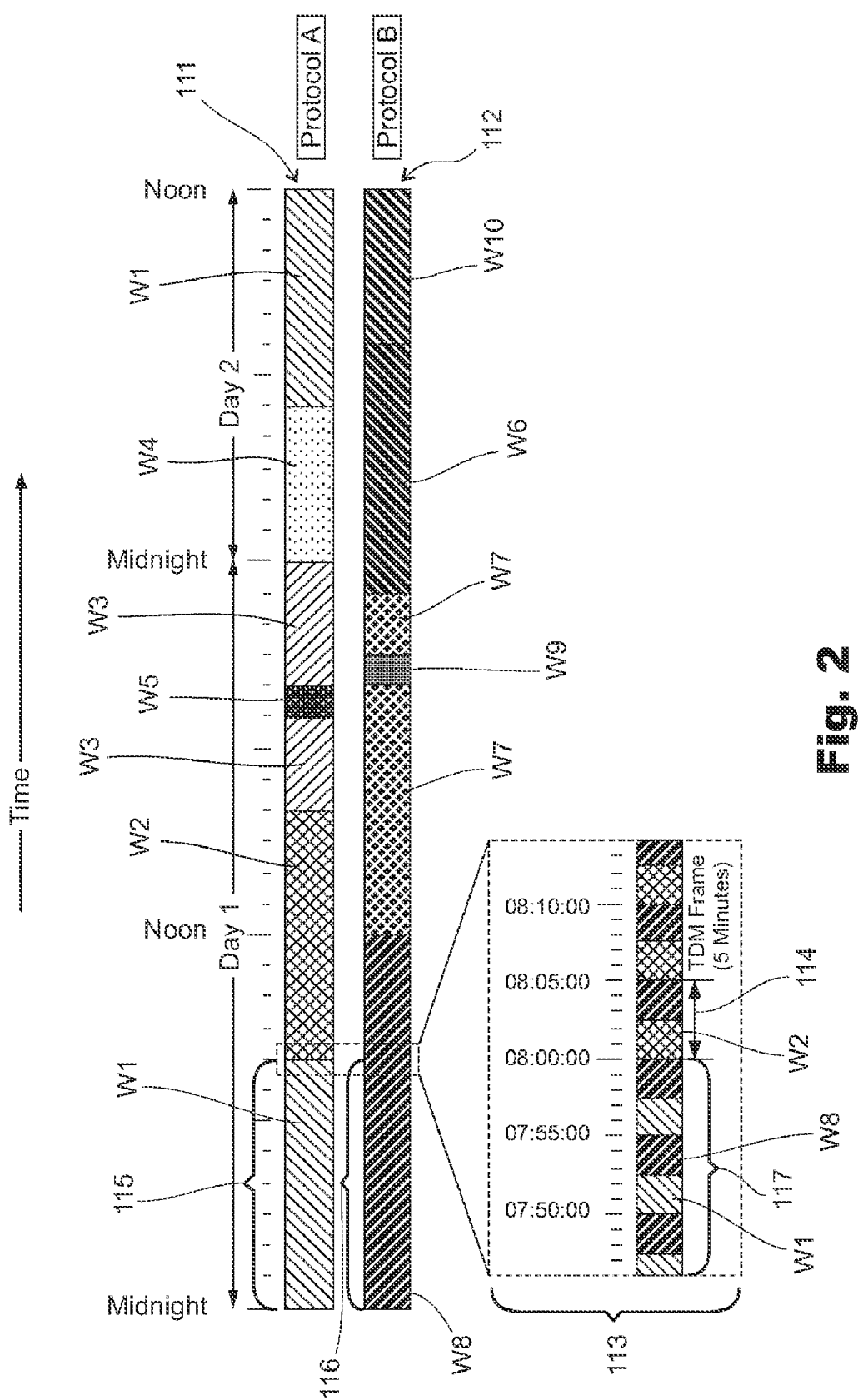
FIG. 2 illustrates an exemplary polysubstance CES protocol, in which two single substance protocols are time-division multiplexed.

In the timelines illustrated in FIG. 2, both Protocols A and B are weighted the same; within each TDM frame the timeslot for each protocol is of equal time length. Each single-substance protocol was given equal weight in the treatment environment. There are cases, however, where the profile of substance abuse warrants weighted presentation of the single-substance protocols within the combined polysubstance protocol. The TDM stream accommodates this by allowing timeslots of different lengths to comprise a TDM frame. The TDM frame still has the same number of timeslots, but the timeslot length for sub-channel A may be different than the timeslot length for sub-channel B, and so forth.

Figure 3:
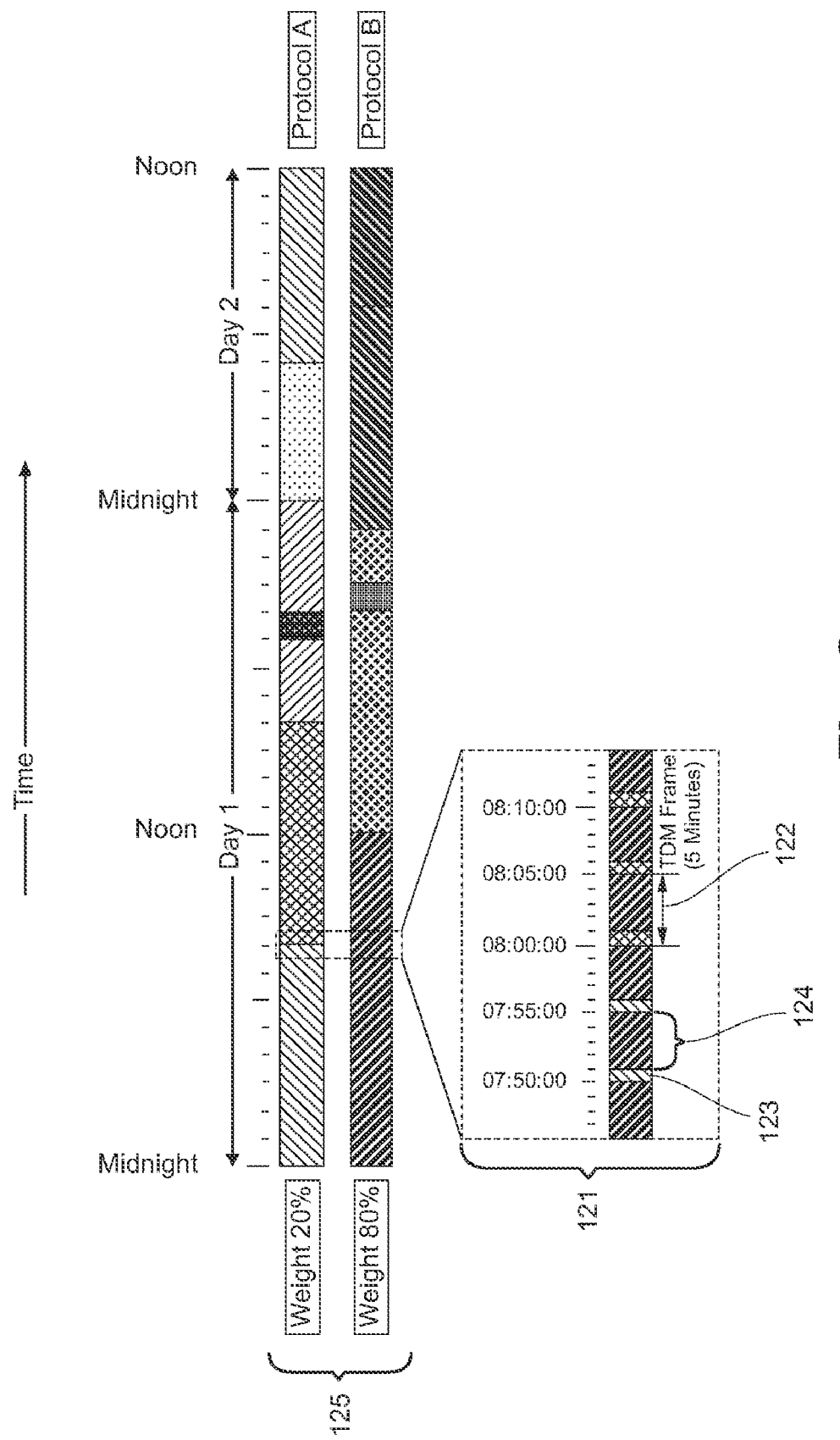
FIG. 3 illustrates another exemplary polysubstance CES protocol, in which two single substance protocols are time-division multiplexed, the two single substance protocols being weighed unequally.

In the alternative embodiment illustrated in FIG. 3, single-substance CES Protocol A and CES Protocol B are combined into poly-substance CES protocol 121. TDM frame length 122 is 5 minutes, timeslot length 123 for Protocol A is 1 minute, and timeslot length 124 for Protocol B is 4 minutes. In this case, respective weights 125 of the Protocols are 1:4.

According to the embodiment illustrated in FIG. 3, each single-substance protocol has a weight that remains uniform throughout the protocol. There are cases, however, where the onset of acute withdrawal symptoms ("AWS") from one substance occurs at a substantially different time in treatment than the onset of AWS from another substance. In such an environment, one may wish to alter the relative weights of the protocols to target the earlier occurring AWS, and then adjust the relative protocol weights when the subsequent AWS commences. Such temporal weighting may be determined based on an analysis of drug test results (e.g., saliva, urine, or blood), oral history, medical history, and prescription history, as well as upon the elimination half-lives of the individual addictive substances in the body. The TDM stream accommodates temporal weighting by first applying a weight function to each sub-channel and then by applying the temporal weight function to each weighted sub-channel in order to calculate the timeslot length for each sub-channel within the TDM frame.

Figure 4:
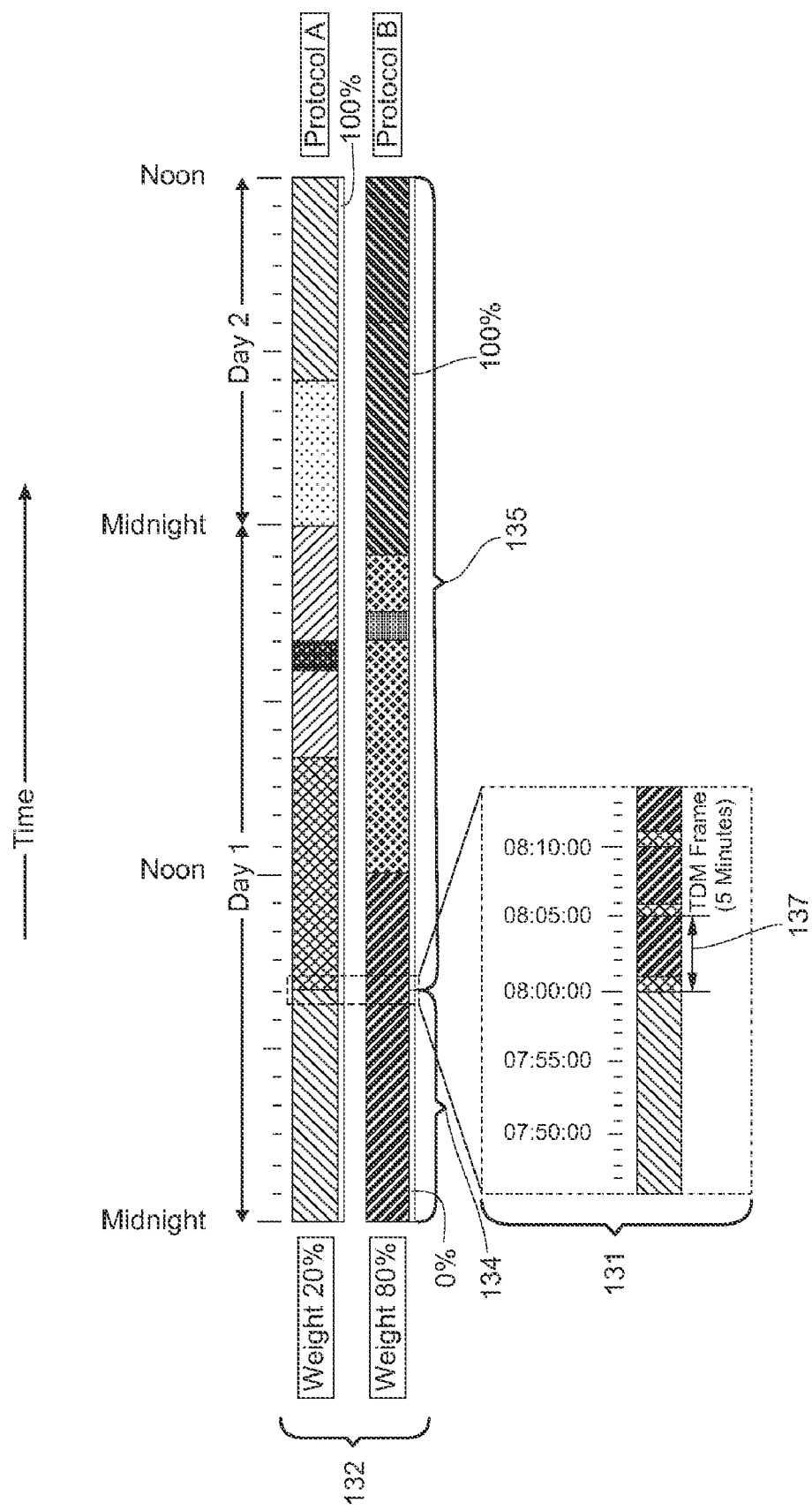
FIG. 4 illustrates yet another exemplary polysubstance CES protocol, in which two single substance protocols are time weighted.

This time weighting is illustrated in FIG. 4, in which the single-substance CES Protocol A and CES Protocol B are combined into polysubstance CES protocol 131. Relative weights 132 of the protocols are 1:4. The temporal weight of Protocol A is set at 100% for its entirety. The temporal weight of Protocol B is set at 0% on Day 1 in time domain 134 from midnight to 8:00 am, at which point it becomes 100% for time domain 135 of the protocol. During the period when the temporal weight of Protocol B is at 0%, the timeslot length for Protocol B is 0 min and the timeslot length for Protocol A is 5 min. Beyond 8:00 am, when the temporal weight of Protocol A and Protocol B are both 100%, the timeslot lengths 137 take on a 1:4 ratio. Temporal weights may vary continuously for the duration of treatment, and may be of any value between 0% and 100%.

In accordance with these principles, polysubstance CES protocols may be customized to the specific needs of an individual patient. These methods support customization of treatment for single individuals and for small or large cohorts with similar addictions. The methods may also be adapted for variations in short-acting and long-acting AWS behaviors, as well as weighting of the treatment strength towards the relevant substances.

Another aspect of the present invention includes a method of compressed data representation or encoding of treatment protocols, including the TDM protocols, which are discussed above. The compressed data encoding method described herein minimizes the time required to download a protocol to a device and minimizes the protocol storage space required within that device.

Since treatment protocols typically are custom-developed for each patient, CES devices typically are designed to receive from an external source and store both the waveform definitions and the treatment protocol. For instance, the CES device may have a port, such as a USB port, for coupling to a USB cable, the other end of which is coupled to a desktop computer. By way of further example, the CES device may have a wireless communications port for communication with a local or remote computer. When a physician has developed a treatment protocol for a particular patient, that patient's CES device is coupled to the computer through a USB cable, and the protocol and the waveform definitions for the waveforms used in that protocol are downloaded to the CES device, which stores them in memory.

Since the CES device is a portable device intended to be carried on the person of an individual, it is important to keep it as small and lightweight as possible and to minimize power requirements. Furthermore, it is desirable to minimize the amount of time required to download treatment protocols. Accordingly, it is desirable to minimize the size of the encoded treatment protocol.

Figure 7:
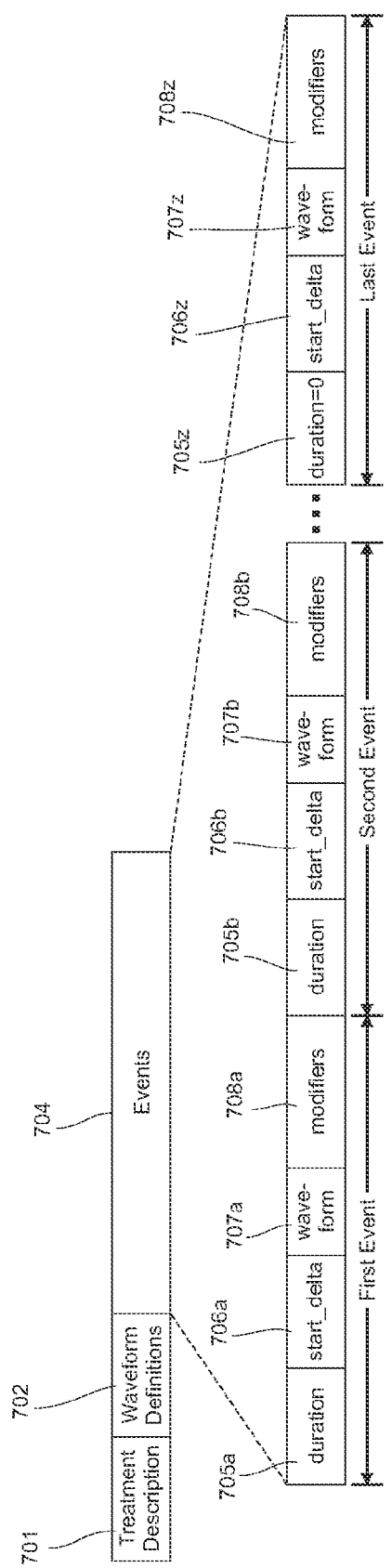
FIG. 7 schematically illustrates a compressed data format suitable for use in encoding CES protocols.

Some treatment protocols may require that multiple waveforms be output simultaneously. These combined treatment protocols may be expressed in the form of multiple individual treatment protocols which are scheduled simultaneously. A treatment protocol can be represented by a timeline showing which waveforms are output by the stimulator as a function of time. FIG. 5 shows the timeline 530 for an exemplary treatment protocol, Protocol A, comprised of a multitude of different waveforms 105 provided sequentially (each different cross-hatching pattern representing a different waveform). Each different waveform (W1, W2, W3, and W5) is designed to have a particular therapeutic effect. FIG. 6 shows a timeline for a combined treatment protocol formed by combining two individual treatment protocols, namely Protocol A 530 and Protocol B 531. To minimize the size of the encoded treatment protocol, a compression method is employed that encodes waveform playback regions based on their relative start times and their durations. FIG. 7 demonstrates an exemplary binary dataset for transmitting a treatment protocol description to a CES device in accordance with the principles of the present invention.

The compressed treatment protocol encoding consists of a first segment (i.e., plurality of bits) defining treatment description 701 that contains information characterizing the treatment or its global properties, a second segment (i.e., plurality of bits) comprising waveform definitions 702 that describe the characteristics of the various waveforms to be used in expressing the treatment protocol, and a third segment (plurality of bits) defining events 704 that express time intervals during which the waveforms described in waveform definitions 702 will be output by the device.

More particularly, an event is provided in the dataset for every waveform to be provided to the electrodes for a continuous duration without cessation of that waveform (as noted above, another waveform could be provided simultaneously without ceasing the first waveform). Thus, for instance, referring to FIG. 6, each of waveforms W1, W2, W3, W5, W7, W8, and W9 corresponds to an event. Each event is described by four data fields. Referring to FIG. 7, the first data field is duration data field 705, which is expressed as a binary number representing a multiple of a chosen granularity. In the examples given, a granularity of one hour has been chosen. The second field is start_delta field 706 which is expressed as the length of time (in units of the chosen granularity) between the start of the previous event (or, in the case of the first event, the beginning of treatment) and the start of the current event. The third data field is waveform field 707, which identifies one of the waveforms described in waveform definitions 702. The fourth data field is modifier field 708 that defines a set of modifiers that can control various aspects of the waveform being output (such as the priority or magnitude given to the output of the waveform relative to other simultaneously output waveforms). The size (in bits) of the duration 705, start_delta 706, waveform 707, and modifiers 708 fields can be chosen to optimize the number of bits required to store typical protocols. In the following example a size of 4 bits has been chosen for the duration, start_delta, and waveform fields, and a size of 8 bits has been chosen for the modifiers field, resulting in 4+4+4+8=20 bits per event. FIG. 7 is illustrated as having events a, b . . . z, although the number of events will vary depending on the desired therapeutic protocol.

As many events as are necessary to describe the treatment protocol may be strung together at the end of the dataset. Particularly, within the events segment of the dataset, the CES device is programmed to understand that every 20 bits is a complete event definition. Hence, the event definition segment of the dataset can be as long or as short as needed and the CES device can easily parse it into the individual events and decode the data in the individual fields for each event until it recognizes a bit pattern indicating the end of the dataset. In this example, an event with a duration of zero is used to signify the end of the event definition segment of the dataset. Since the event definition segment of the dataset is the last segment of the dataset, an event with a duration of zero also indentifies the end of the protocol definition, i.e., the end of the dataset.

Figure 8:
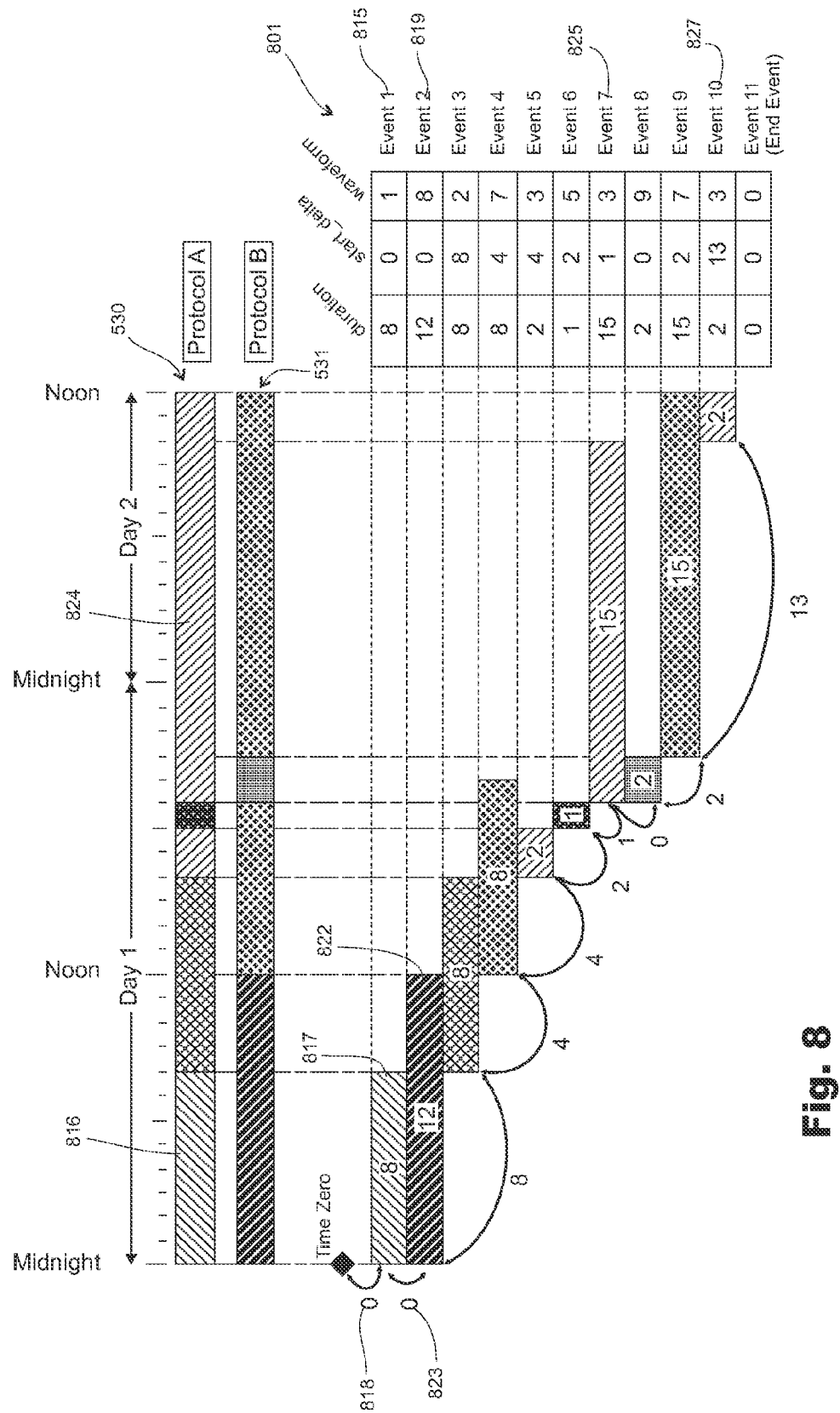
FIG. 8 schematically illustrates generation of data in the compressed format from a CES protocol.

FIG. 8 illustrates the dataset encoding the combined treatment protocol illustrated in FIG. 6 consisting of the two individual protocols, Protocol A 530 and Protocol B 531. For clarity, the two protocols as represented in FIG. 6 are shown again at the top of FIG. 8. Beneath them, each event (a waveform segment) is shown again on its own individual row. Finally, to the right of each row in table 801 is shown the duration field value, start_delta data field value, and waveform field value for describing that event. The field values are shown in decimal, however, it will be understood that they would actually be represented in binary in the actual binary dataset.

Figure 9:
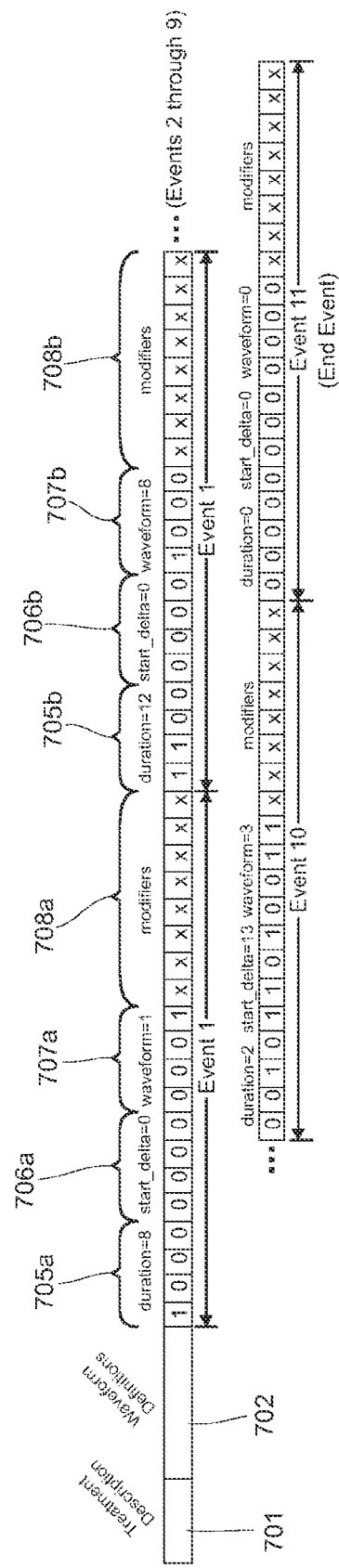
FIG. 9 illustrates the bitwise data represented in an exemplary dataset.

For simplicity, the modifier field is not shown in FIG. 8, but there would be one for each event definition in the actual dataset. If there were no modifiers for the waveform segment, then its value may be set to zero. FIG. 9 shows the actual dataset as it would appear in a binary data stream (although the modifier field as well as the treatment description segment and waveform definition segment are represented with generic data).

In the actual dataset (see FIG. 9), the waveform events in the two individual protocols, Protocol A and Protocol B, are ordered chronologically in order of their start times. In cases where two waveform events (one from each of the two protocols) start at the same time, the ordering of those two events relative to each other may be arbitrary. FIG. 9 illustrates that the encoding method includes a linear data format that encodes co-linear (i.e., simultaneous) events.

Referring to FIG. 8, the first event, Event 1 (815), represents the first waveform in Protocol A (816), waveform W1, which starts at midnight and ends at 8 am. Thus, the event has a length of 8 hours (817), so its duration field is set to 8 (binary 1000). Further, Event 1 starts 0 hours after start 818 of the treatment, so its start_delta field is set to 0 (binary 0000). The event encodes waveform W1, so its waveform field is set to 1 (binary 0001).

The second event, Event 2 (819), represents the next chronologically occurring waveform in the combined treatment protocol, which, in this case, is waveform W8 of Protocol B. The event has a length of 12 hours (822), so its duration field is set to 12 (binary 1100). The event starts 0 hours after previous event 823, so its start_delta field is set to 0 (binary 0000). The event encodes waveform W8, so its waveform field is set to 8 (binary 1000).

A review of FIG. 8 will show that the rest of the event definitions follow the same encoding scheme.

A protocol might contain a waveform for which the playback duration exceeds the maximum expressible event duration. In the example illustrated in FIG. 8, the duration field was chosen to have a width of 4 bits, so the maximum expressible duration is $2^4-1=15$ hours. However, the last waveform 824 of Protocol A has a duration of 17 hours, which exceeds the maximum expressible value of 15 hours. In such a case, the event may be split and expressed as multiple events of less than or equal to the maximum event duration. Thus, as seen in FIG. 8, Event 7 (825) encodes the first 15 hours of waveform W3, and Event 10 (827) encodes the last 2 hours of waveform W3.

In this manner, a single dataset having linearly organized data can represent multiple sequential or simultaneous waveforms. As noted above, simultaneous waveforms may be time-division multiplexed.

Figures 10, 11:
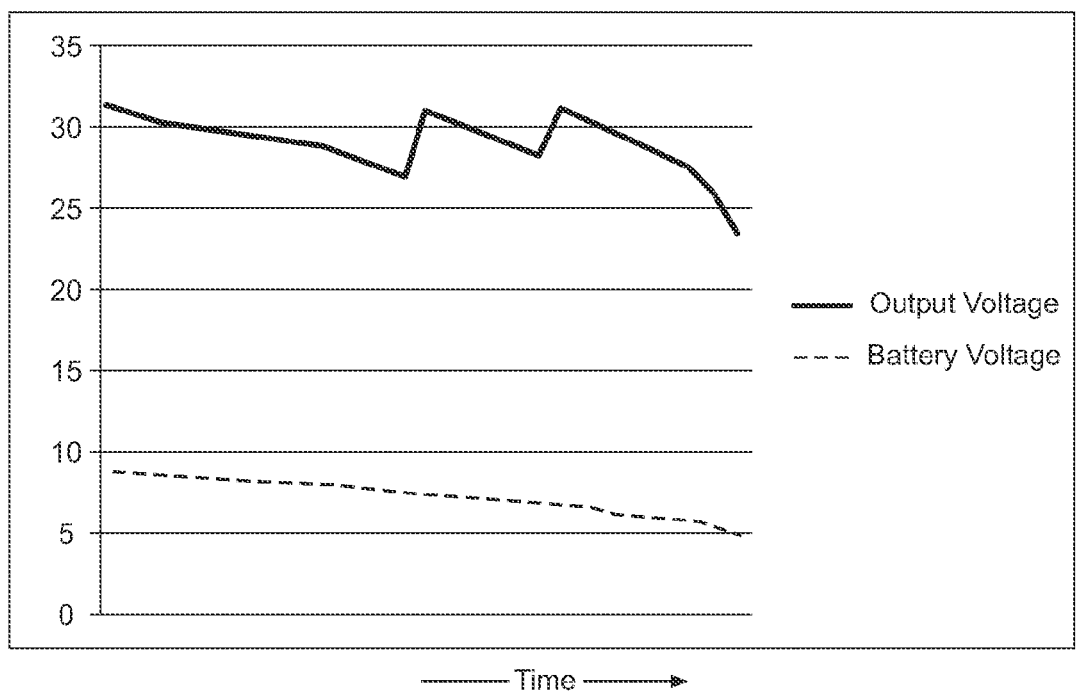
FIG. 10 illustrates the decay in output voltage as battery voltage drops, as is found in prior art CES devices.
FIG. 11 illustrates the stable output voltage of the improved CES devices described herein.

Another aspect of the present invention is an improved CES apparatus for carrying out the methods described above. Heretofore existing CES devices suffer from a drop in output voltage as the power supply, typically a 9V battery, is depleted. FIG. 10 illustrates the output voltage drop over time. In order to compensate for the voltage drop, the patient manually turns up the intensity with a control knob. If the output voltage drop occurs while the patient is sleeping, then the therapeutic effect may be diminished, and a need exists for improved CES devices that passively maintain a steady output voltage. The present invention provides an improved CES device in which this output voltage drop phenomenon is mitigated, as illustrated in FIG. 11. In the improved device, the output voltage remains substantially constant over the entire useful service life of the battery. When the battery is completely spent, the voltage drops precipitously (see FIG. 11), at which time the battery is simply replaced.

It should be understood that in certain embodiments the invention does not seek to eliminate patient control over the CES device. Indeed, it may be desirable for the patient to have some degree of control. For example, the patient may become accustomed to the sensation of a given output voltage over time and therefore turn up the voltage over time to maintain maximal therapeutic value.

At the most fundamental level, a CES apparatus comprises (1) a power source, such as a battery, (2) a signal generator for generating a control signal corresponding to the desired signal waveform for treatment, (3) a line driver that receives the power signal from the battery and the control signal and modulates the power signal from the battery as dictated by the control signal, and (4) a pair of electrodes coupled to the output of the line driver. Commonly, the apparatus also comprises a potentiometer or other means for allowing the patient to adjust the signal level delivered to the electrodes to a comfortable level for the particular patient. This signal level is herein termed an amplitude envelope for clarity since the therapeutic signal per se is a waveform, the amplitude of which varies in time as dictated by the control signal. It is the overall relative voltage amplitude range (or envelope) of this signal that is controllable by the patient.

Figure 12:
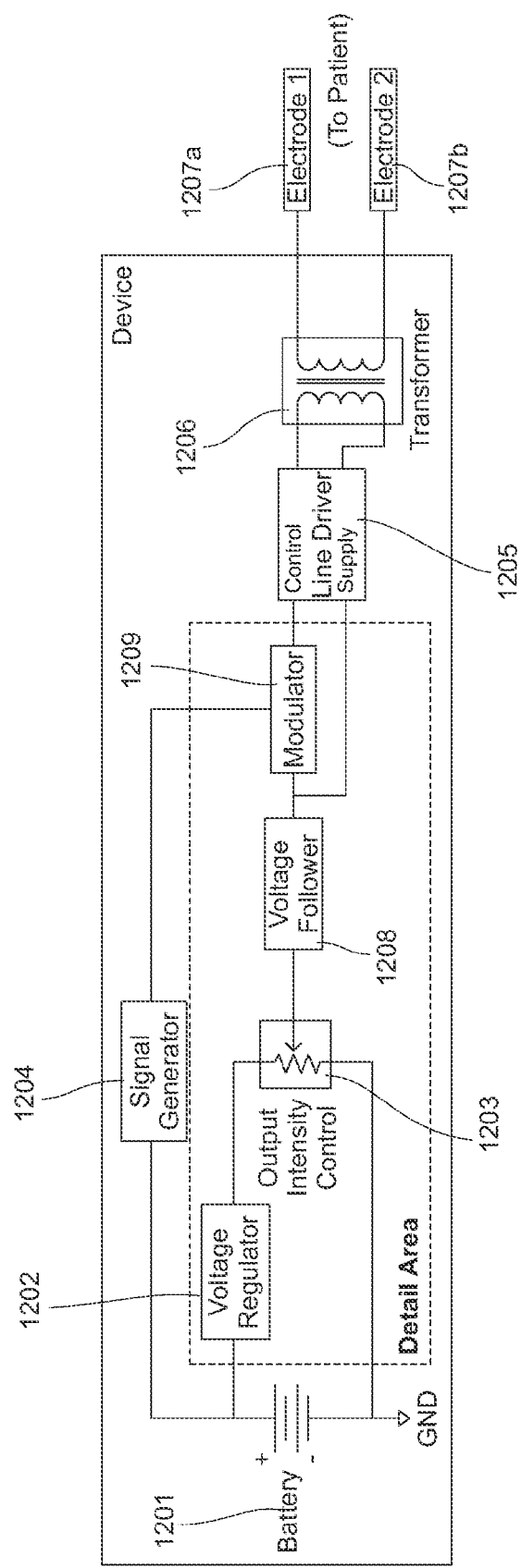
FIG. 12 is a block diagram of an exemplary CES device.

FIG. 12 illustrates one possible embodiment of a CES device illustrating circuitry for generating the therapeutic output waveform signal in accordance with an aspect of the present invention in which the amplitude envelope of the waveform signal is maintained at a constant level for as long as possible despite a decreasing battery output voltage in order to eliminate the effect of battery drainage on the therapeutic signal. When the battery power drops below some minimum level such that there is not enough power for the voltage regulator to generate the desired output voltage amplitude, the output voltage will decay, alerting the patient (through diminished sensation of intensity) that the battery needs to be replaced or recharged as the case may be. However, while the device was operational, the patient received the therapeutic signal with the desired voltage envelope consistently over the useful life of the battery.

FIG. 12 illustrates one possible embodiment of a CES device with such regulation of the amplitude of the therapeutic output signal. In this embodiment, voltage regulator 1202, is coupled to the output voltage of battery 1201 and the output of voltage regulator 1202 is supplied to one terminal of an output intensity control circuit, such as potentiometer 1203, coupled across the terminals of battery 1201. Battery 1201 also provides power to signal generator 1204, which is configured to provide a control signal for controlling the waveform output to the electrodes to be the desired therapeutic waveform. The control signal output from signal generator 1204 is provided to a control input of line driver circuit 1205 and the regulated voltage is supplied to the supply input of line driver 1205. Line driver 1205 modulates the supply signal as dictated by the control signal to generate an output signal that is supplied to electrodes 1207a, 1207b, through transformer 1206. In this particular embodiment, voltage follower 1208 is interposed between the power generation portion of the circuitry (essentially battery 1201, voltage regulator 1202, and potentiometer 1203) and line driver 1205 to help isolate the power supply circuitry from noise or other signals on electrodes 1207 and line driver 1205.

Furthermore, a modulator may be interposed between the output of the signal generator and the control input terminal of the line driver. Specifically, as illustrated in FIG. 12, modulator 1209 receives the regulated output voltage from the power supply circuitry and modulates it in accordance with the control signal. This feature can be included to amplify the control signal, for instance, to a voltage range commensurate with the voltage supplied at the supply input terminal of the line driver, which is necessary or desirable for certain types of line drivers.

Figure 13:
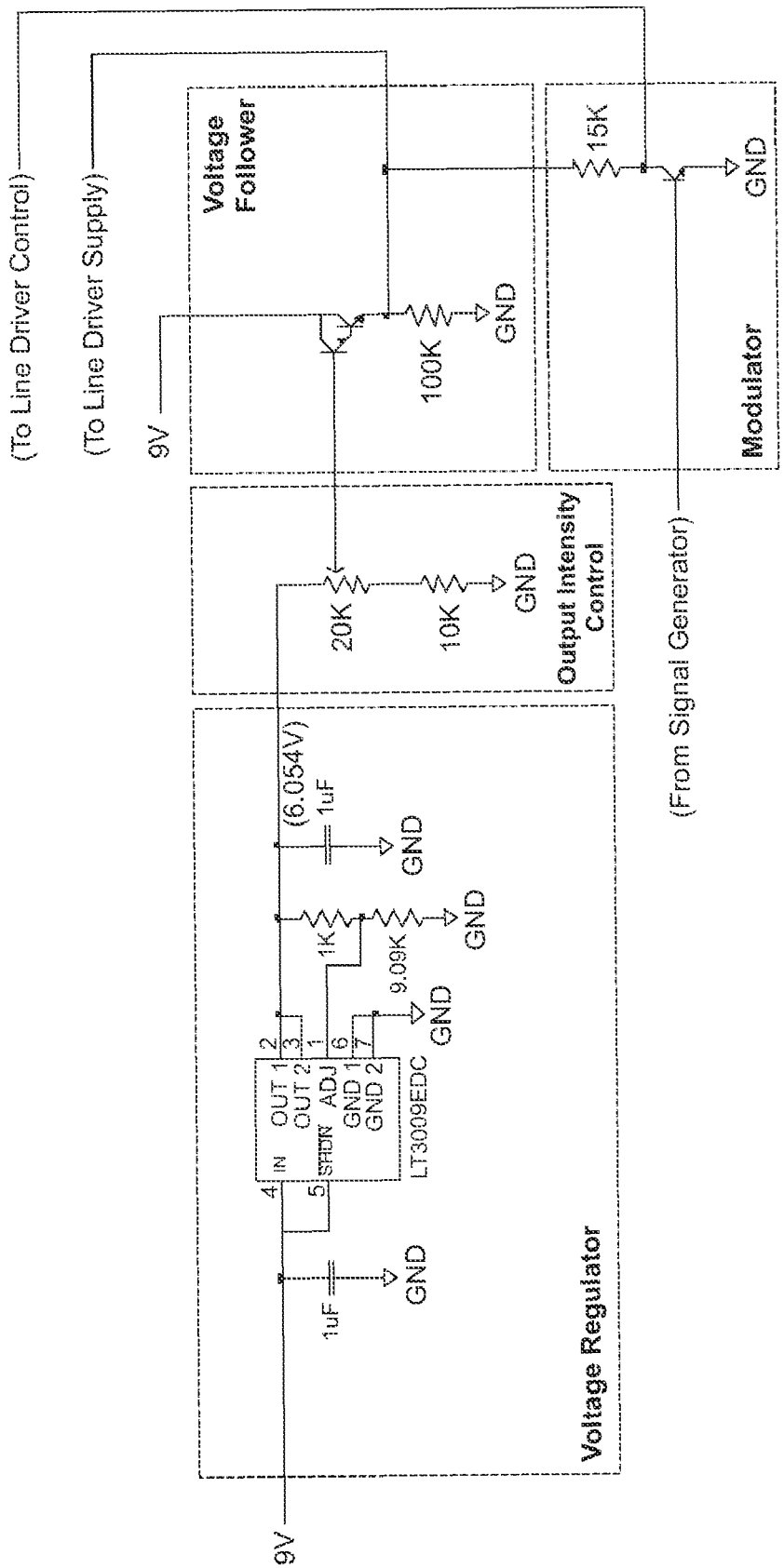
FIG. 13 is a circuit diagram of a preferred embodiment of a CES device.

So that the block diagram illustrated in FIG. 12 may be better understood, some exemplary electronic components corresponding to the block diagram in an actual circuit are depicted in circuit diagram in FIG. 13.

Figures 14A, 14B, 14C, 14D, 14E, 14F, 14G, 14H, 14I:
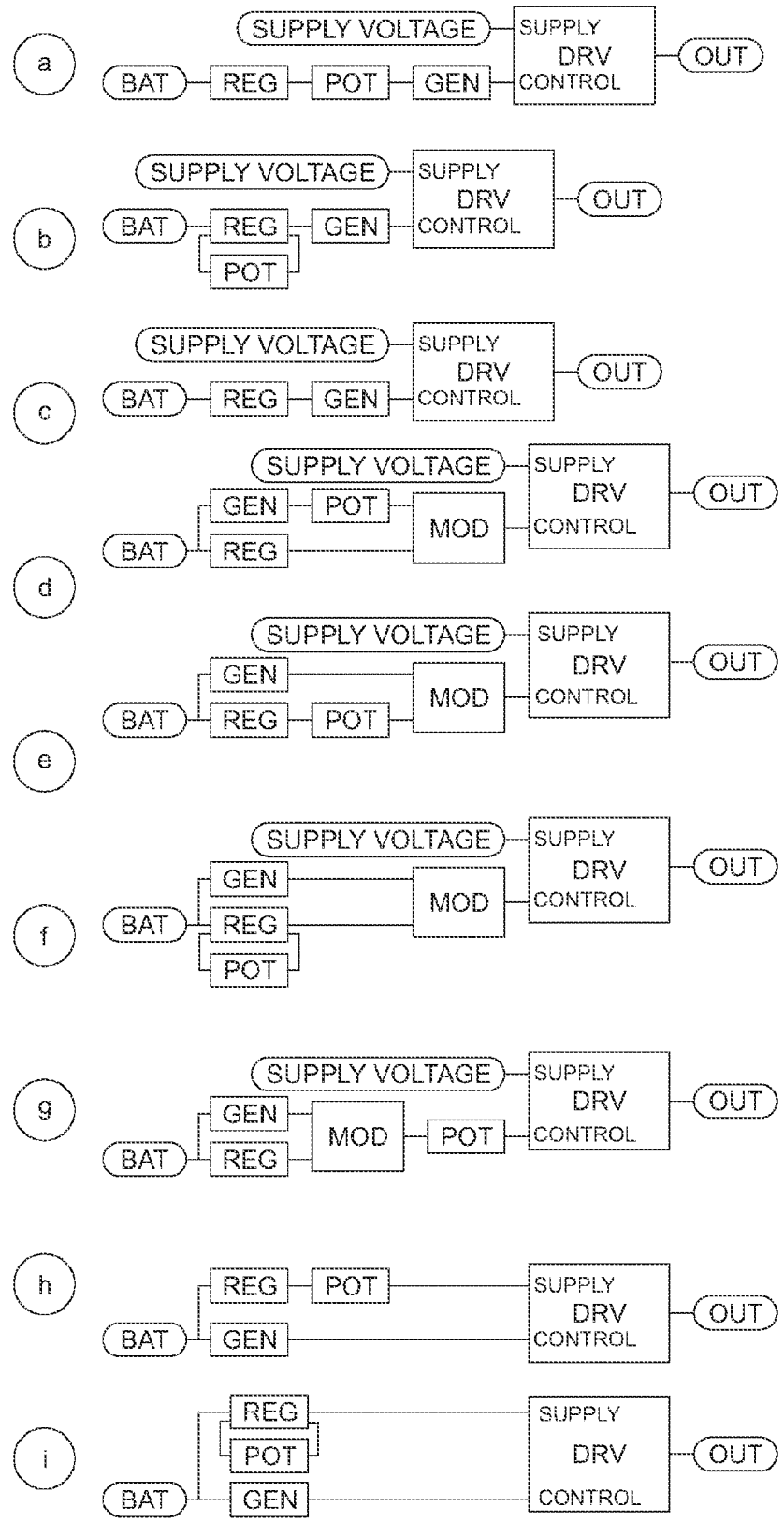
FIGS. 14(a)-(i) are block diagrams of alternative CES devices.

FIG. 12 and FIG. 13 show merely one exemplary embodiment. Many other configurations are possible, some of which are illustrated in FIGS. 14(a)-(i). FIGS. 14(h) and 14(i) demonstrate two alternative embodiments. FIG. 14(h) is quite similar to the embodiment illustrated in FIG. 12, except that the optional voltage follower and modulator are omitted. FIG. 14(i) is similar to FIG. 14(h), except that the potentiometer is coupled in parallel with the voltage regulator rather than in series with it.

FIGS. 14(a)-(g) illustrate a series of possible embodiments for use in connection with line drivers of a different type than described above in connection with FIGS. 12, 14(h), and 14(i). Particularly, the line drivers in FIGS. 14(a)-(g) generate an output voltage that is a scaled version of the voltage at the control input (essentially using the voltage provided at the supply terminal as a rail voltage).

Thus, in all of the embodiments of FIGS. 14(a)-(g), the supply terminal of the line driver is supplied with a supply voltage that may be the regulated output voltage of the battery, but may also be the unregulated output of the battery, or a completely different power source such as another battery. Because of the different nature of the line drivers of FIGS. 14(a)-(g), in these embodiments, it is the control signal supplied to the control signal input terminal of the line driver that is regulated, not the input of the supply terminal.

Thus, for instance, in FIG. 14(a), the output of the battery is applied to the voltage regulator and, therefrom, to the potentiometer, and then into the signal generator before being supplied to the control input terminal of the line driver. FIG. 14(b) shows an alternate embodiment similar to FIG. 14(a) except with the potentiometer coupled in parallel with the voltage regulator. FIG. 14(c) shows another embodiment, similar to the embodiment of FIG. 14(a), but with the potentiometer omitted. FIG. 14(d) illustrates a different embodiment in which the output of the signal generator is supplied to the potentiometer and, there through, to one input of a modulator. The other input of the modulator is coupled to the regulated battery power. The modulator essentially amplifies the control signal before providing it to the control input of the driver. FIG. 14(e) is similar to the embodiment of FIG. 14(d), except that the potentiometer is placed in the path between the regulator and the modulator, rather than in the path between the signal generator and the modulator. This circuit will operate essentially identically to the circuit of FIG. 14(d). FIG. 14(f) is similar to the embodiment of FIG. 14(e), except that the potentiometer is coupled in parallel with the voltage regulator, rather than in series with it (similar to the difference between the embodiments of FIGS. 41(h)-(i)). Finally, FIG. 14(g) shows an embodiment similar to the embodiments of FIGS. 14(e)-(f), except that the potentiometer is coupled into the signal path between the output of the modulator and the control input of the driver. Many other embodiments are possible. For instance, a voltage follower such as shown in FIG. 12 may be added to any of the embodiments illustrated in FIGS. 14(a)-(i).

EXAMPLES

Two patients ("Patient 1" and "Patient 2") were treated with a polysubstance protocol ("Protocol C"), which was composed of three multiplexed single-substance CES protocols administered over several days. During the course of treatment, each patient wore a CES device as described herein. The device was portable, and it was carried with the patient throughout the day including while the patient was sleeping at night. The polysubstance protocol was delivered to the patients' mastoid process via two electrodes. Throughout the treatment protocol, each patient was asked to self-assess the relative intensity of several acute and chronic withdrawal symptoms from a value of zero to three for each category of symptoms listed in Table 1, below.

TABLE 1

| Withdrawal Symptoms. |
| --- |
| 0 Agitation/Restlessness |
| 1 Body Aches/Pains |
| 2 Chills |
| 3 Craving |
| 4 Diarrhea |
| 5 Feeling Down/Depressed |
| 6 Feelings of Unreality |
| 7 Head/Body/Hand Tremors |
| 8 Headache |
| 9 Irritable/Nervous |
| 10 Low Energy/Fatigue |
| 11 Nausea/Vomiting |
| 12 Palpitations/Pounding Heart |
| 13 Poor Concentration |
| 14 Shakiness |
| 15 Stomach Cramps |
| 16 Suspicious/Paranoid |
| 17 Sweating |
| 18 Teary Eyes/Runny Nose |
| 19 Tingling in Fingers/Toes |
| 20 Unsteadiness/Feeling of Motion |
| 21 Visual Disturbances |

The sum of the scores for each category was recorded 3 times a day (morning, afternoon, and evening) producing a total Withdrawal Severity Scale ("WSS") score. The WSS scores for each patient during this course of treatment are listed in Table 2, below.

TABLE 2

| WSS Scores. | | | | | | |
| --- | --- | --- | --- | --- | --- | --- |
| Day | 1 | 1 | 1 | 2 | 2 | 2 |
| Time | Morning | Afternoon | Evening | Morning | Afternoon | Evening |
| Patient 1 | 53 | 52 | 56 | 62 | 57 | 56 |
| Patient 2 | 40 | 14 | 18 | 14 | 12 | 10 |
| Day | 3 | 3 | 3 | 4 | 4 | 4 |
| Time | Morning | Afternoon | Evening | Morning | Afternoon | Evening |
| Patient 1 | 57 | 54 | 60 | 61 | 61 | 45 |

TABLE 2-continued

| | | | WSS Scores. | | | |
|---|---|---|---|---|---|---|
| Patient 2 | 11 | 7 | 3 | 12 | 10 | 6 |
| Day | 5 | 5 | 5 | 6 | 6 | |
| Time | Morning | Afternoon | Evening | Morning | Afternoon | |
| Patient 1 | 38 | 34 | 33 | 8 | 8 | |
| Patient 2 | 6 | 4 | 2 | — | — | |

Figure 15:
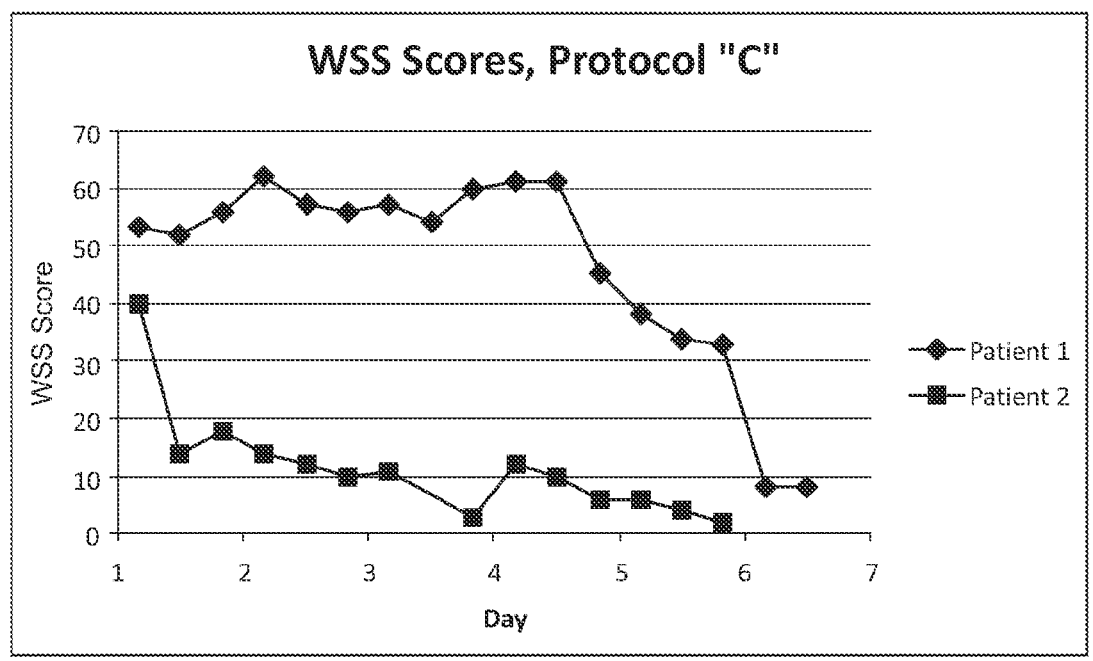
FIG. 15 is a graph of human clinical data for two addicted persons who have been treated in accordance with the therapeutic methods described herein.

The reduction of WSS score over time, which is illustrated in FIG. 15, demonstrated that the polysubstance Protocol C was effective for detoxification from and amelioration of the symptoms of acute and chronic withdrawal from simultaneous multiple addictive substances. In addition to the objective WSS data, the patients also reported that their subjective assessment of their own treatments were successful.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The invention claimed is:

1. A cranial electrostimulation apparatus comprising
a power supply configured to generate a DC power signal wherein said power supply is a battery;
a signal generator configured to generate a control signal for modulating said power signal corresponding to a waveform adapted to provide therapeutic value to a patient;
a voltage regulator coupled to receive said DC power signal from said power supply and output a regulated DC voltage signal;
wherein said voltage regulator maintains said regulated DC voltage within a predetermined range as said DC power signal changes over the useful service duration of said power supply;
a line driver configured to receive as inputs said control signal and said regulated DC voltage signal and generate an output waveform signal by modulating said regulated DC power signal with the control signal;
electrodes coupled to receive said output waveform signal; and
wherein said control signal is adapted to encode a therapeutic protocol for one of treatment and prevention of symptoms of withdrawal from one or more addictive substances.

2. A cranial electrostimulation apparatus comprising
a power supply configured to generate a DC power signal wherein said power supply is a battery;
a signal generator configured to generate a control signal for modulating said power signal corresponding to a waveform adapted to provide therapeutic value to a patient;
a voltage regulator coupled to receive said DC power signal from said power supply and output a regulated DC voltage signal;
wherein said voltage regulator maintains said regulated DC voltage within a predetermined range as said DC power signal changes over the useful service duration of said power supply;
a line driver configured to receive as inputs said control signal and said regulated DC voltage signal and generate an output waveform signal by modulating said regulated DC power signal with the control signal;
electrodes coupled to receive said output waveform signal; and
a voltage follower circuit coupled between said voltage regulator circuit and said line driver.

3. A cranial electrostimulation apparatus comprising
a power supply configured to generate a DC power signal wherein said power supply is a battery;
a signal generator configured to generate a control signal for modulating said power signal corresponding to a waveform adapted to provide therapeutic value to a patient;
a voltage regulator coupled to receive said DC power signal from said power supply and output a regulated DC voltage signal;
wherein said voltage regulator maintains said regulated DC voltage within a predetermined range as said DC power signal changes over the useful service duration of said power supply;
a line driver configured to receive as inputs said control signal and said regulated DC voltage signal and generate an output waveform signal by modulating said regulated DC power signal with the control signal;
electrodes coupled to receive said output waveform signal; and
a modulator circuit coupled to receive said control signal and said regulated DC voltage signal and output to said line driver a modified control signal comprising said regulated DC voltage signal modulated by said control signal.

4. A cranial electrostimulation apparatus comprising
a power supply configured to generate a DC power signal wherein said power supply is a battery;
a signal generator configured to generate a control signal for modulating said power signal corresponding to a waveform adapted to provide therapeutic value to a patient;
a voltage regulator coupled to receive said DC power signal from said power supply and output a regulated DC voltage signal;

wherein said voltage regulator maintains said regulated DC voltage within a predetermined range as said DC power signal changes over the useful service duration of said power supply;

a line driver configured to receive as inputs said control signal and said regulated DC voltage signal and generate an output waveform signal by modulating said regulated DC power signal with the control signal;

electrodes coupled to receive said output waveform signal; and a multiplexer configured for time-division multiplexing a plurality of waveforms into said output waveform signal.

5. A method of encoding a definition of a protocol for generating an analog signal for cranial stimulation comprised of a plurality of different waveforms combined sequentially or simultaneously, the method comprising creating a dataset comprising
 a first segment defining each waveform of the plurality of waveforms; and
 a second segment comprising an event definition for each different waveform segment presented without cessation in said analog signal, the event definitions organized sequentially in the dataset according to the relative time at which the corresponding waveform segment starts within the protocol;
wherein each event definition comprises
 a duration field disclosing the duration of said waveform segment;
 a start_delta field disclosing the start time of the event, start time defined as a delay period following the start time of an immediately preceding event definition in said dataset and by zero for the first event definition in said dataset; and
 a waveform identifier field identifying one of the plurality of waveforms for the waveform segment.

6. The method according to claim 5, wherein each event definition further comprises a modifier field disclosing special properties of said waveform segment.

7. The method according to claim 6, wherein, if a waveform segment starts at the same time as the waveform segment defined in the immediately preceding event definition, the corresponding start_delta field is set to zero.

8. The method according to claim 6, further comprising an end bit sequence representing the end of said event definition segment of said dataset.

9. The method according to claim 8, wherein said end bit sequence comprises an event definition in which said duration field contains a value corresponding to a duration of zero.

10. The method according to claim 9, wherein said event definition segment succeeds the waveform definition segment of said dataset and said end bit sequence further indicates the end of said dataset.

11. The method according to claim 6, further comprising a treatment description segment.

12. The method according to claim 5, wherein each data field in the event definitions has a single predetermined number of bits.

13. The method according to claim 12, wherein said duration field represents the duration of said waveform segment as a number representing a number of predetermined time intervals and wherein, when a duration of a waveform segment exceeds the maximum amount of time that can be represented by corresponding predetermined number of bits dedicated to that data field, said waveform segment is represented in said dataset by a plurality of event definitions.

14. A method of downloading a definition of a protocol for generating an analog signal for cranial stimulation comprised of a plurality of different waveforms combined sequentially or simultaneously to a cranial electrostimulation device, the method comprising connecting the CES device to a source of protocol definitions; and receiving from the source a dataset comprising
 a first segment defining each waveform of the plurality of waveforms; and
 a second segment comprising an event definition for each different waveform segment presented without cessation in said analog signal, the event definitions organized sequentially in the dataset according to the relative time at which the corresponding waveform segment starts within the protocol;
wherein each event definition comprises
 a duration field disclosing the duration of said waveform segment;
 a start_delta field disclosing the start time of the event, start time defined as a delay period following the start time of an immediately preceding event definition in said dataset and by zero for the first event definition in the dataset; and
 a waveform identifier field identifying one of the plurality of waveforms for the waveform segment.

15. The method according to claim 14, wherein each data field in the event definitions has a single predetermined number of bits.

16. The method according to claim 15, wherein said duration field represents the duration of said waveform segment as a number representing a number of predetermined time intervals and wherein, when a duration of a waveform segment exceeds the maximum amount of time that can be represented by corresponding predetermined number of bits dedicated to that data field, said waveform segment is represented in said dataset by a plurality of event definitions.

17. The method according to claim 16, further comprising an end bit sequence representing the end of said event definition segment of said dataset, wherein said end bit sequence comprises an event definition in which said duration field contains a value corresponding to a duration of zero.

* * * * *